United States Patent [19]

Merkl

[11] 4,053,570

[45] Oct. 11, 1977

[54] ALUMINUM HALOHYDRATE

[76] Inventor: George G. Merkl, 46 Sunset Court, Haworth, N.J. 07641

[21] Appl. No.: 758,344

[22] Filed: Jan. 10, 1977

Related U.S. Application Data

[60] Division of Ser. No. 439,628, Feb. 4, 1975, Pat. No. 4,038,373, which is a continuation-in-part of Ser. No. 45,527, June 11, 1970, abandoned, and Ser. No. 127,351, March 23, 1971, abandoned, said Ser. No. 45,527, is a continuation-in-part of Ser. No. 859,703, Sept. 22, 1969, said Ser. No. 127,351, is a continuation-in-part of Ser. No. 859,703, , and Ser. No. 45,527.

[51] Int. Cl.$^2$ .............................. C01F 7/00; C01F 7/48
[52] U.S. Cl. ...................................... 423/462; 423/495
[58] Field of Search .............................. 423/462, 495

[56] References Cited

U.S. PATENT DOCUMENTS

| | | | |
|---|---|---|---|
| 2,876,163 | 3/1959 | Garizio et al. | 423/462 X |
| 3,128,223 | 4/1964 | Rosenberg et al. | 423/462 X |
| 3,523,153 | 4/1970 | Holbert et al. | 423/462 X |
| 3,638,327 | 2/1972 | Levy et al. | 423/462 X |

OTHER PUBLICATIONS

"Basic Aluminum Compounds" by Hideo Tanabe, American Perfumer and Cosmetics, vol. 77, Aug. 1962, pp. 23–30.
Chemical Abstracts, 1961, vol. 61, pp. 14195 and 14196.
"Aluminum Chlorohydrate, New Antiperspirant Ingredient" by T. Govett et al., The Amer. Perfumer and Essential Oil Review, Apr. 1947 (4 pages).
Fiat Final Report No. 788, p. 7.

*Primary Examiner*—Edward Stern

[57] ABSTRACT

An aluminum halohydrate is formed by first preparing a reactive aluminum by permeating highly pure aluminum with mercury in the presence of a hydrogen ion source and then contacting the reactive aluminum with a source of iodine, chlorine, bromine or fluorine in the presence of water. The products obtained show high stability, uniformity from batch to batch, and a pH of about 4.3.

5 Claims, 4 Drawing Figures

ALUMINUM CHLOROHYDRATE

ALUMINUM HALOHYDRATE

CROSS REFERENCE TO RELATED APPLICATIONS

This application is a division of application Ser. No. 439,628, filed Feb. 4, 1974, now U.S. Pat. No. 4,038,373, which application is a continuation-in-part of both of the two co-pending patent application Ser. No. 45,527 filed June 11, 1970, now abandoned and application Ser. No. 127,351 filed March 23, 1971, now abandoned. Application Ser. No. 45,527 is a continuation-in-part of application Ser. No. 859,703 filed Sept. 22, 1969. Application Ser. No. 127,351 was a continuation-in-part of both the application Ser. No. 859,703 and application Ser. No. 45,527.

Reference is made to the following co-pending applications: Reactive Metals, Ser. No. 211,979 filed Dec. 27, 1971, now abandoned; Aluminum Hydrates and Salts of Carboxylic Acids, Ser. No. 255,757 filed May 22, 1972, now abandoned; Metal Hydrates and Salts of Carboxylic Acids, Ser. No. 255,758 filed May 22, 1972, now abandoned; and Composition of Matter and Apparatus and Method for the Same, Ser. No. 176,907 filed Sept. 1, 1971.

BACKGROUND OF THE INVENTION

The present invention relates to methods of forming selected aluminum halohydrates and to the aluminum halohydrates formed thereby.

The present invention relates more particularly to the methods of forming aluminum iodohydrate, aluminum chlorohydrate, aluminum bromohydrate, and aluminum fluorohydrate.

Generally, aluminum halohydrates have found substantial commercial usages in a wide variety of fields, including use as an active ingredient in body deodorants, tawing salts, an for this impregnation of textiles to impart water repelling properties. In addition, aluminum halohydrates are also used for the preparation of absorption agents or catalytically active substances. Many other commercial uses for the chemicals are well known.

Prior art methods for preparing aluminum halohydrates often include the step of reacting an aluminum halide salt, such as aluminum fluoride, aluminum chloride, aluminum bromide or aluminum iodide with water and metallic aluminum. The process described in the U.S. Pat. No. 3,476,509 includes the use of water soluble thallium compound with a pH of between 2.5 and 4.4 at an elevated temperature in the order of 70° C to 105° C. The aluminum hydrate formed from an aluminum halide usually shows traces of the aluminum halide. This has been recognized to be a very serious problem especially for aluminum chlorohydrate when used as an antiperspirant because the aluminum chloride hydrolyzes to hydrochloric acid and results in severe skin irritation. The presence of the aluminum halide also tends to make the aluminum halohydrates hydroscopic.

The article entitled, "Basic Aluminum Compounds" by Hideo Tanable in *The American Perfumer and Cosmetics*, Vol. 77, August 1962 pages 25-30 provides a review of known methods for preparing aluminum halohydrates. On page 26, Tanabe presents four methods by way of equations (5), (6), (7), and (8). The four methods are briefly given herein for reference:

1. More than an equivalent amount of metallic aluminum is reacted with an acid, or metallic aluminum is reacted with an aluminum salt with a catalyst of mercury, iron, or copper:
2. More than an equivalent amount of aluminum hydroxide is reacted with an acid;
3. An alkali is added to an aluminum salt solution; and
4. An aqueous solution of an aluminum halide is passed through an anion exchange resin.

On page 26, Tanabe presents the general formula $Al_{2+n}OH_{3n}X_6$ and indicates that when "n" is large, the soluton is slightly turbid but can be made clear by filtration with carbon powder. Tanabe continues with an analysis of the aluminum chlorohydrate and states that each of the four reactions results in a basic aluminum ion which condenses gradually into a polynuclear ion and this condensation is influenced by various conditions such as temperature, time and the the value of "n". Thus, the aluminum chlorohydrate reported by Tanabe appears to show instability with both temperature and time. An eariler Tanable article in *Pharm. Soc. Japan*, 75 page 868 (1955) is directed to the study of these instabilities.

Another earlier article by Tanabe, in *Pharm. Soc. Japan*, 74, page 868 (1954) states explicitly that the properties of aluminum chlorohydrate varies with the method of preparation.

SUMMARY OF THE INVENTION

One of the principal objects of the Invention is to provide a method for preparing aluminum iodohydrate, aluminum chlorohydrate, aluminum bromohydrate and aluminum fluorohydrate by the steps of first permeating aluminum having a plurality by weight of at least 99.98% with mercury in the presence of a hydrogen ion source, such as an acid, and then contacting the permeated aluminum with an appropriate halogen ion source in the presence of an excess of water compared to the halogen, in accordance with the formula $Al_2(OH)_5X$ where "X" corresponds to the selected halogen.

Another object of the present invention is to obtain novel aluminum iodohydrate, aluminum chlorohydrate, aluminum bromohydrate and aluminum fluorohydrate compounds exhibiting novel properties.

A further object of the present invention is a method of preparing selected aluminum halohydrates having a desired ratio between the aluminum and halogen atoms.

Yet another object of the present invention is to provide a method for preparing aluminum iodohydrate, aluminum chlorohydrate, and aluminum bromohydrate by the use of the corresponding gas in the presence of water.

Yet another object of the present invention is a method for preparing aluminum iodohydrate from iodine crystals in water.

Further objects and advantages of the invention will be set forth in part in the following specification and in part will be obvious therefrom without being specifically referred to, the same being realized and attained as pointed out in the claims hereof.

The present invention accordingly comprises the several steps and the relation of one or more of such steps with respect to each of the others, all as exemplified in the following detailed disclosure, and the scope of the application of which will be indicated in the claims. Furthermore, the products obtained are novel and exhibit properties which are superior to known corresponding products. For example, the products obtained are water-clear when dried to a solid, are soluble in water, and are not hygroscopic. In addition, the aluminum iodohydrate, aluminum chlorohydrate, and aluminum bromohydrate exhibit superior bacterialcidal properties.

BRIEF DESCRIPTION OF THE DRAWINGS

For a fuller understanding of the nature and object of the invention, reference should be had to the following detailed description, taken in connection with the accompanying drawings, in which.

THE INVENTION

Figure 1:
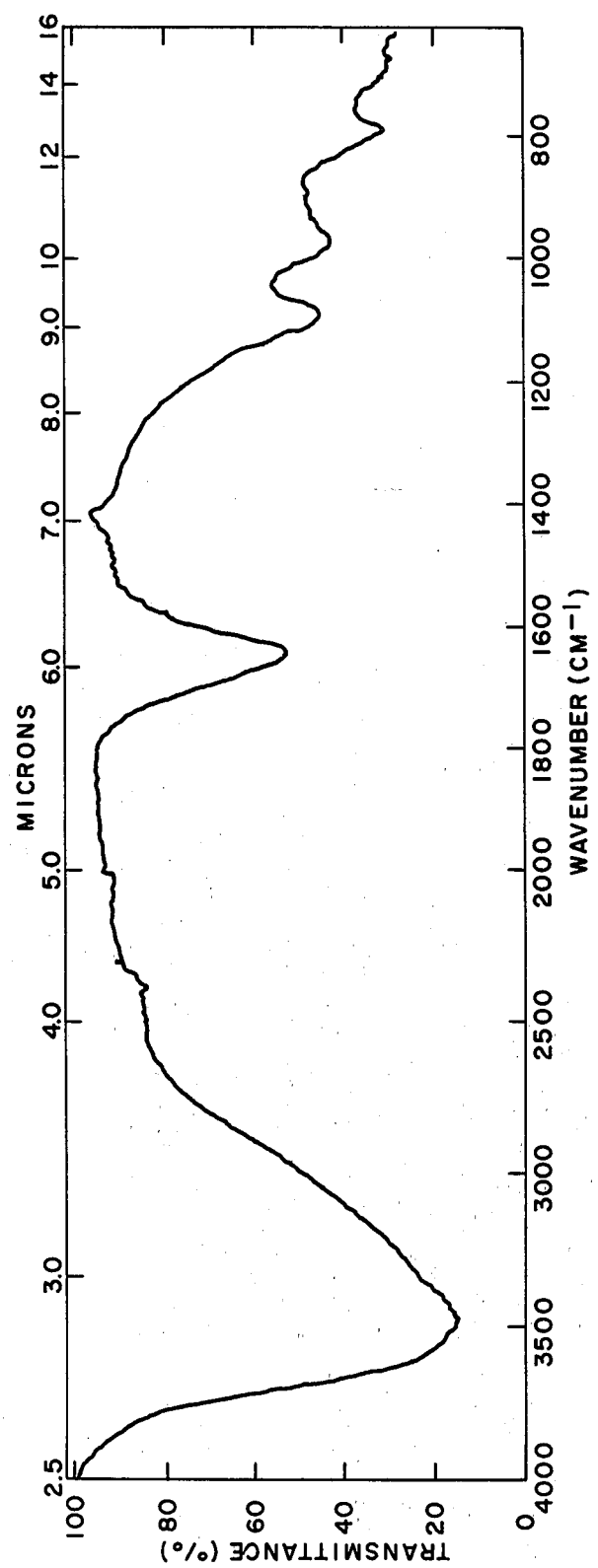
FIG. 1 is an infrared spectra response for aluminum iodohydrate prepared according to the present invention.
Figure 2:
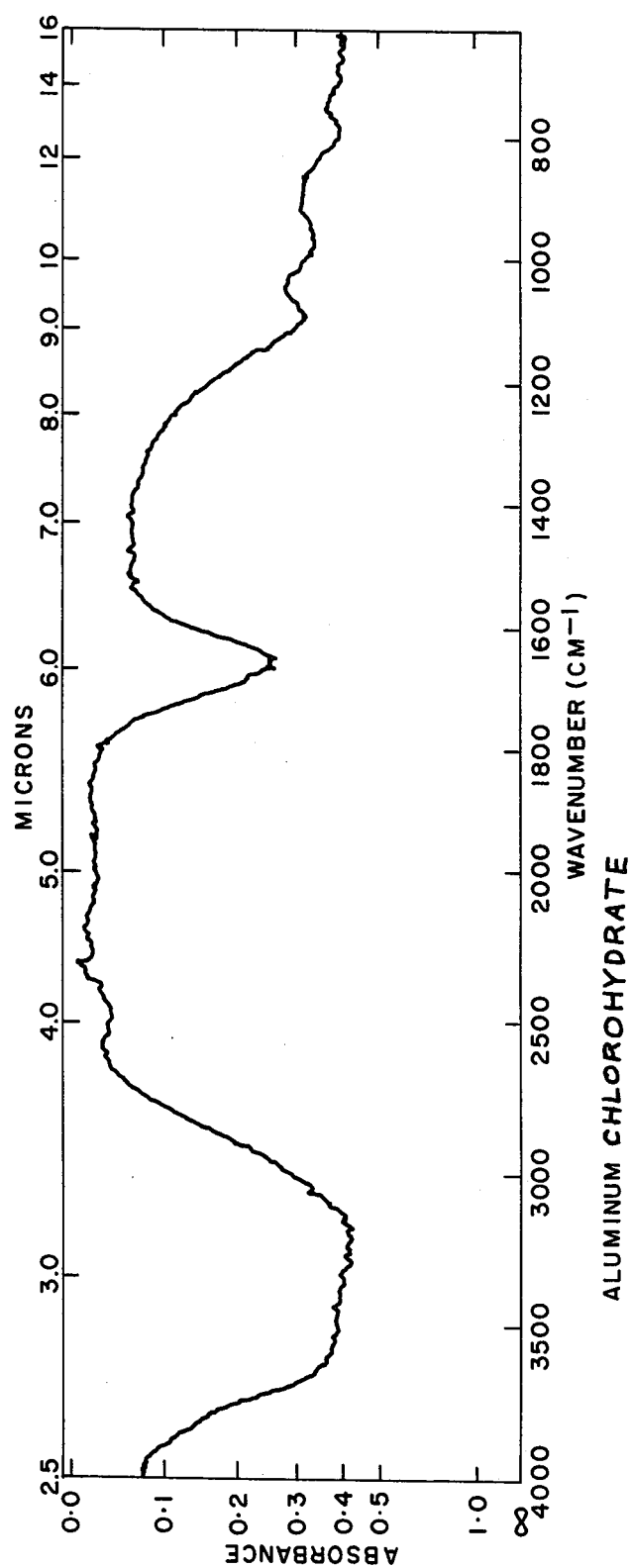
FIG. 2 is an infrared spectra response for aluminum chlorohydrate prepared according to the present invention.
Figure 3:
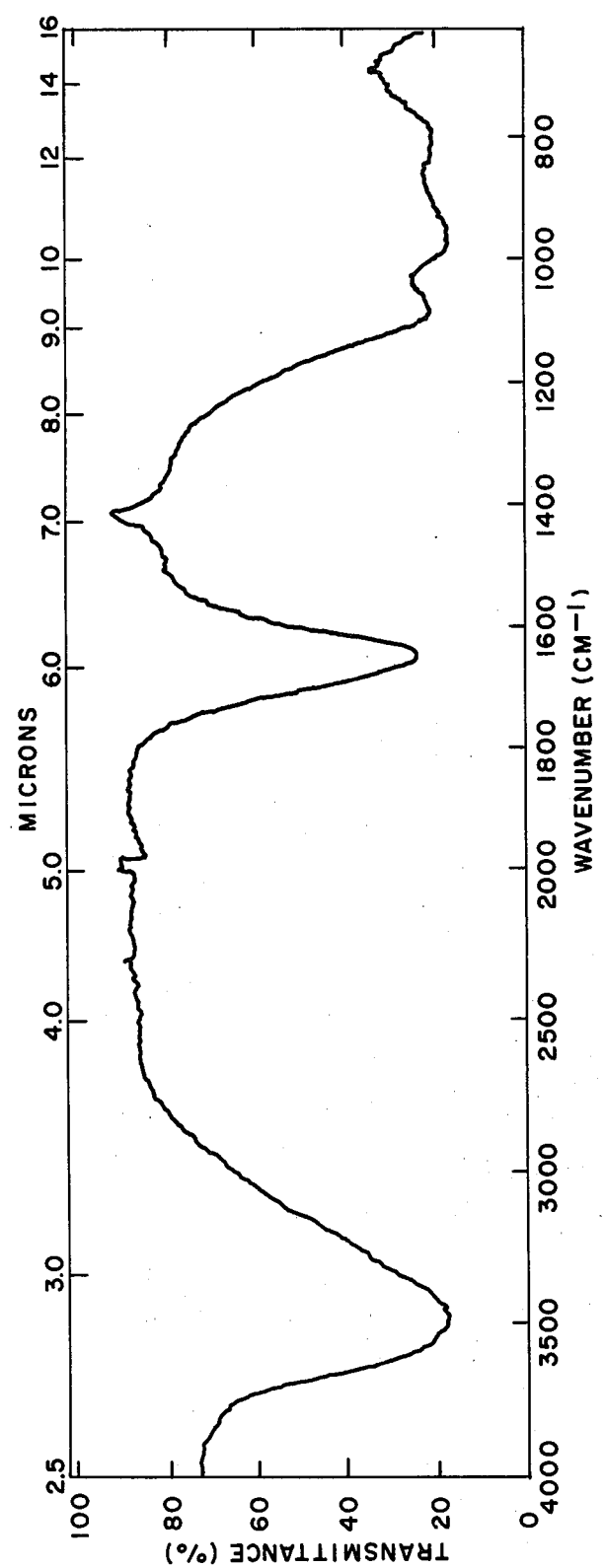
FIG. 3 is an infrared spectra response for an aluminum bromohydrate prepared according to the present invention.
Figure 4:
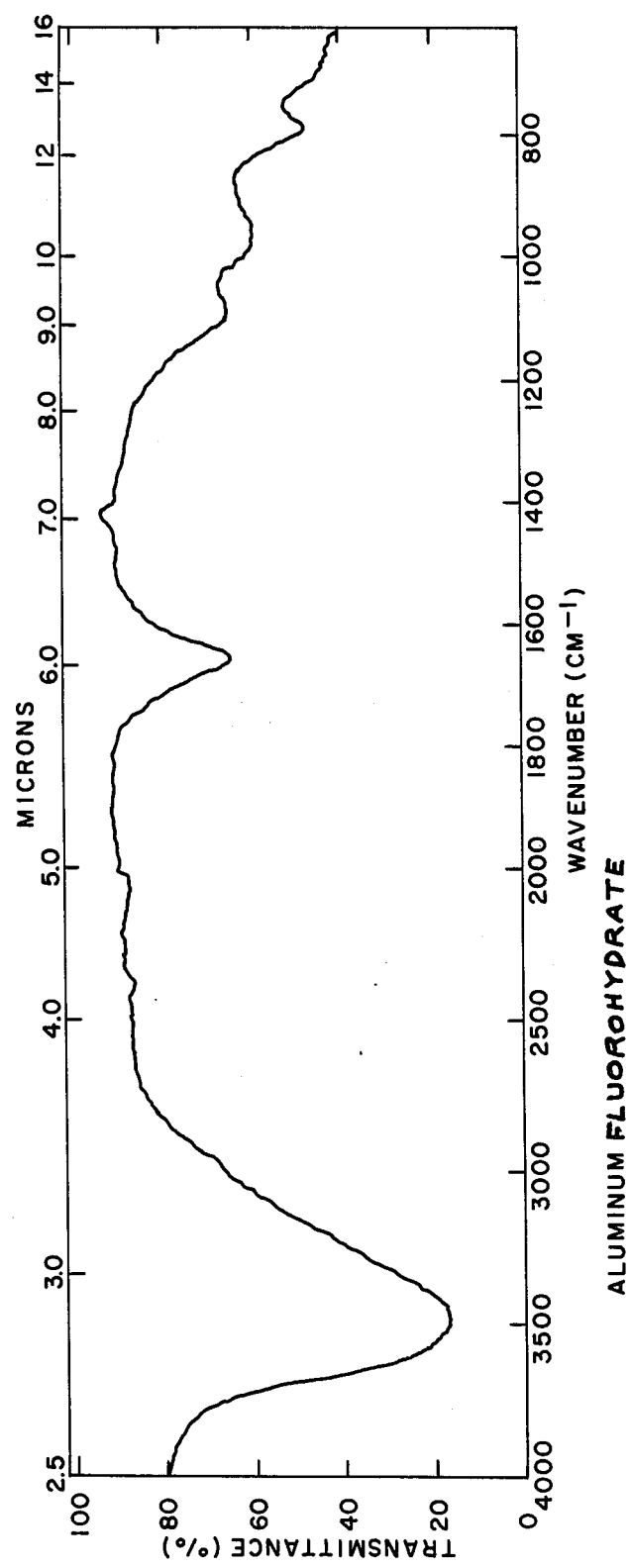
FIG. 4 is an infrared spectra response for an aluminum fluorohydrate prepared according to the present invention.

The present invention if focused on the utilization or the remarkable properties of a reactive aluminum described in application Ser. No. 211,979, now abandoned.

Generally, a reactive aluminum is prepared by permeating highly pure aluminum in the presence of a hydrogen ion source with mercury. The hydrogen ion source can be an inorgaic acid, such as hydrochloric acid or hydrobromic acid or the like, or an organic acid, such as citric acid or acetic acid, or the like. The reactive aluminum in an alkali solution such as water and sodium hydroxide will serve as an hydrogen ions source for the formation of another reactive aluminum.

It should be understood that the term "highly pure" herein means a purity greater than 99.98% by weight.

The concentration of the acid employed can cover the broadest range. The choice of the hydrogen ion source such as an acid will depend upon the product to be formed and the concern over impurities.

It is preferable to prepare a highly pure aluminum rod for the reaction by at least partially stripping the aluminum oxide coating which usually has formed on the surface due to exposure to air and moisture. Of course, other than a rod shape can be used. If the aluminum rod has been stripped, hot water can serve as a hydrogen ion source, although the reaction time is long. Otherwise, it may be desirable to start out with an acid to strip off the oxide coating on the aluminum rod in order to initiate the reaction as quickly as possible. Of course, the aluminum rod may be stripped mechanically with sandpaper or a file or the like.

The inter-reaction which occurs between the aluminum, the mercury and the acid, gives rise, at the start, to the formation of large bubbles which rise up to the surface through the acid. After a while, it will be observed that instead of large bubbles forming at the top of the aluminum rod and then breaking free and rising to the surface of the acid, tiny bubbles will be eminating from many parts of the upper surface of the rod. The occurrence of the multitude of tiny bubbles indicates that the rod is becoming converted to receive aluminum as herein used.

Generally, the rod will take up or absorb from 0.1% to 5% by weight of the mercury depending upon the length of time the reaction is permitted to continue. A range of 2% to 3% by weight of the mercury is satisfactory for many application. The maximum mercury content is about 5% by weight.

The reaction can be stopped on the one hand due to increase in weight or the rod due to the absorption of the metal or on the other hand due to the production of a multitude of tiny bubbles for a period of ten to fifteen minutes. Another basis is to test the rod by immersing it in water hydrolysis of the water to absence.

A reactive aluminum as described, displays surprisingly active catalytic properties not at all suggested by the prior art. The reactive aluminum possesses an altered physical structure and my be used as an activator or initiator. After grain alignment, the reactive aluminum becomes an open matrix where the boundaries have expanded.

The amount of the mercury in the aluminum can be varied in accordance with applications. In general, if a high percent of the mercury of weight is desired, quick cooling of the reactive aluminum after formation will prevent the squeezing out of the mercury due to an exothermic reaction and lattice expansion. Water or alcohol is convenient for this purpose. In cases where it is desired to reduce the amount of, mercury from several percent by weight to 0.1% by weight, for example the reactive aluminum can be heated to squeeze out the mercury.

Certain impurities such as copper and iron, inhibit the formation of a reactive aluminum and so should be avoided in the aluminum. Some of the impurities which inhibit or promote the reaction are given in the aforementioned Reactive Metals application. But, small amounts of the inhibitors can be tolerated for certain applications.

DESCRIPTION OF THE PREFERRED EMBODIMENTS

For a fully understanding of the invention certain embodiments have been selected for more detailed description.

Generally, a reactive aluminum is reacted with water and a selected source of chlorine, bromine, iodine or fluorine. In many cases, it is convenient to use an acid form of the selected halogen. Sometimes, it is convenient to use a gaseous form of the selected halogen, such as chlorine gas, or bromine gas iodine vapors. A further possibility in the use of ground iodine crystals in water.

Basically, the amount of water present compared to the available halogen atoms can be determined from the formula: $Al_2(OH)_5Q$; Q corresponds to the halogen: chlorine, bromine, iodine of fluorine. It is preferable to use more water than the stoichiometric equivalent of the formula in order to be assured of having sufficient hydroxyl groups available.

The ratio of the aluminum atoms to the halogen atoms varies from the ratio of 2:1. It is highly significant that the ratio of 2:2:1 for aluminum chlorohydrate and 2.4:1 for aluminum bromohydrate can be obtained by the present invention. Also, a ratio of 2.7:1 for aluminum iodohydrate has been obtained by the present methods. Surprisingly, the product obtained by the present methods even for high ratios of aluminum to halogen is water clear.

In addition, the products obtained by the present methods show a stable pH of about 4.2 to about 4.3 in contrast to products obtained by prior art methods which have a pH of approximately 3.9.

In carrying out the present methods, it is desirable to cool the reaction to below 100° F in order to avoid the incidental formation of an aluminum halide. The presence of an aluminum halide in prior art products is considered highly undesirable. However, products obtained by the present methods are non-hydroscopic and are therefore far more suitable for many applications where prior art products were unsuitable. For example, the present aluminum chlorohydrate is well suited use as an underarm deodorant even in for high concentrations, since the absence of aluminum chloride avoids the formation of hydrochloric acid and irritation to human skin. Tests with even relatively concentrated solutions have verified this for human use.

Another significant advantage of the present product is that the present products becoe micronized after spray drying and at least 99% will pass a 325 mesh. Prior art products require additional treatment in order to become micronized after spray drying. This may be related to the fact that prior art products have at least 14% moisture content after spray drying in contrast to the present products which have only about an 8% moisture content after spray drying.

The aluminum used in the present method preferably is high purity aluminum having a purity of 99.99% by weight and is readily available in rod form but, of course, other shapes can be used. It is preferable to prepare the reactive aluminum with the halogen acid corresponding to the aluminum halohydrate to be formed in order to maintain high purity. Repeated washing of a reactive aluminum can be used for cleansing the reactive aluminum of potential impurities. Usually, it is highly desirable to form the aluminum halohydrate with a high degree of assurance that no mercury will appear in the product. This can easily be achieved by using a reactive aluminum having a mercury content by weight such that the mercury by weight in the initial reactive aluminum corresponds to less than approximately 3% by weight of the reactive aluminum after completion of the reaction. It is known that the reactive aluminum retains mercury up to the approximate saturation point of about 5% by weight. Thus, calculations can show the amount of aluminum which will be consumed to obtain the desired aluminum to halogen ratio for the available halogen and these calculations can guide the selection of the total weight of the reactive aluminum used and the mercury content thereof. This is another surprising feature contributing to the high purity of the product obtained by the present methods.

The aluminum iodohydrate, aluminum bromohydrate, and aluminum chlorohydrate prepared by the present methods exhibit surprisingly good anti-microbial properties. Standard tests are used to determine the anti-microbial number, namely the concentration to completely destroy pseudomonas and aeruginosia in 10 minutes but not 5 minutes. The aluminum iodohydrates was effective at dilutions in the order of 1000:1 to 600:1 and the aluminum chlorohydrate was effective at a dilution in the order of 1000:1. The Aluminum bromohydrate was effective at a dilution of approximately 100:1. The aluminum iodohydrate showed suprisingly superior anti-microbial activity even compared to IOPREP (trademark), a well known pre-surgical antiseptic. The antimicrobial dilution of the aluminum iodohydrate against stabhylococcus and pseudomonas was 400:1 in each case as compared to the IOPREP which was 100:1 in each case. Furthermore, one part of a 25% concentration aluminum iodohydrate was combined with 4 parts of Ivory (trademark) soap and was found effective against staphylococcus even after being diluted 80 times. The solution was also effective against pseudomonas but only for a dilution of 40 times.

Therefore, a further step in the present invention includes using aluminum iodohydrate prepared in accordance with the present invention for its anti-microbial properties.

With regard to usual properties, it is noted that the aluminum bromohydrate is suprisingly well suited for fireproofing such things as wood, clothes and paper. The fireproofing properties can be imparted either by spraying a solution of the aluminum bromohydrate on the object or soaking the object therein. Naturally, other methods may be use.

After preparing an aluminum halohydrate according to the present methods, it may be desirable to enrich the hydroxyl content of the aluminum halohydrate. The enrichment of the hydroxyl content may be carried out by utilizing the product obtained as described in applicant's co-pending patent application Ser. No. 176,907. Briefly, the product of application Ser. No. 176,907 is obtained by placing highly pure aluminum in contact with mercury and an acid with a part of the aluminum exposed to air. The aluminum can be in the form of a rod with the mercury covering about half of the rod lying therein. A novel product forms on the aluminum exposed to the air. The temperature of the rod should preferably be maintained below 105° F. Cooling can be accomplished many different ways but one convenient way is to contact the aluminum with a large pool of mercury and use only a small amount of acid to just bearly cover the mercury. The mercury helps to conduct heat away from the rod and therefore cools the rod. An operating temperature of about 90° F is preferable. The novel product obtained is extremely rich in hydroxyl groups and can be added to the aluminum halohydrate and mixed with or without heating to obtain a hydroxyl enriched aluminum halohydrate.

Sometimes it is desirable to obtain an aluminum halohydrate involving at least two different halogen atoms. This can be easily accomplished by the present methods by using, for example, two different acids such as hydrochloric acid and hydrobromic acid. Other variations include, for example, hydrofluoric acid with chlorine gas pumped therethrough in the presence of an immersed reactive aluminum.

The products obtained by the present method are polymeric in nature and the above noted formula should not be considered restrictive because the number of aluminum atoms in a unit may exceed the number two and can easily be 4 or 6 with a corresponding increase, but not necessarily proportional, number of hydroxyl and halogen atoms included. Furthermore, with regard to the formula, the hydroxyl content could be less than "5" depending upon the available quantity of hydroxyl groups.

Sometimes an alcohol soluble product is desired. Such a product can be obtained by the use of water and alcohol but some instabilities over extended periods of time have been noted for aluminum chlorohydrate.

EXAMPLES

Illustrative non-limiting examples of the practice of the invention are set forth below. Numerous other examples can readily be evolved in the light of the guiding principles and teachings contained herein. The examples are intended merely to illustrate the invention and not in any sense to limit the manner in which the invention can be practiced. The parts and percentages recited herein and all through this specification, unless specifically provided otherwise, refer to parts by weight and percentages by weight.

EXAMPLE 1

The procedure for preparing an aluminum clorohydrate illustrates some general rules. Typically, it is convenient to use a mass of aluminum equal to that needed to obtain a desired ratio. The aluminum chlorohydrate is prepared by first forming a mercury treated reactive aluminum rod and then reacting the reactive aluminum with hydrochloric acid. A rod of 54 grams of aluminum having a purity of 99.98% by weight is permeated in the presence of hydrochloric acid with mercury so that the permeated mercury is between 1% to 3% by weight of the rod. Then, the reactive aluminum is immersed in 87 grams of 1.5N hydrochloric acid. Generally, the acid can range between 0.5N and 2N or higher. It is preferable to maintain the temperature of the reaction below about 100° F in order to avoid the possibility of forming aluminum chloride or a product which does exhibit a stable chemical property. Generally, a temperature of 200° F or higher should be avoided so that halides are not formed.

EXAMPLE 2

The reactive aluminum rod of Example 1 is immersed in a solution of 126 grams of approximately 38% concentration hydrochloric acid and 300 grams of water. Again, the reaction temperature is maintained below 100° F. After approximately 72 hours, the liquor contains about 50% by weight solid aluminum chlorohydrate with the balance being water. The aluminum to chlorine ratio is approximately 2.04:1.

EXAMPLE 3

The reactive aluminum rod of Example 1 is immersed in 250 grams of 50% by weight methanol with the balance being water; then, 36 grams of chlorine gas is bubbled therethrough over a period of approximately 24 hours. The product obtained had an aluminum to chlorine ratio of approximately 1.86:1.

EXAMPLE 4

The reactive aluminum of Example 1 is immersed in 87 grams of 38% by weight concentration of hydrochloric acid mixed with 150 grams of methanol and 300 grams of water. The temperature is maintained below 100° F by cooling. After 72 hours, the liquor contained approximately 50% by weight aluminum chlorohydrate with the balance being mainly methanol. The aluminum to chlorine ratio was approximately 1.92:1. When the liquor was permitted to dry, alcohol soluble crystals were obtained.

EXAMPLE 5

An aluminum chlorohydrate is prepared with the reactive aluminum of Example 1 is immersed in 250 grams of water which has been twice distilled and then chlorine gas is bubbled through the water, preferably so that the bubbles collide with the reactive aluminum. It may be desirable to recirculate the gas which has not been reacted. 36 grams of chlorine reacted over a period of approximately 72 hours producing a liquor having 46% by weight of aluminum chlorohydrate. A reactive aluminum of 59 grams yields a product with a ratio of aluminum to chlorine 2.2:1.

EXAMPLE 6

An aluminum iodohydrate is prepared by using 59 grams of the reactive aluminum of Example 1 in 435 grams of water and 127 grams of powdered iodine. The water and iodine agitated so that the iodine all contacts are the reactive aluminum. A product with an aluminum to iodine ratio of 2.7:1 is obtained.

EXAMPLE 7

An aluminum bromohydrate is prepared by immersing a 64 gram reactive aluminum in 600 grams of water and introducing 80 grams of bromine gas into the water so that the bubbles contact the reactive aluminum. The gas flow should be regulated to occur over a period of several days. A product with an aluminum to bromine ratio of 2.4:1 is obtained.

EXAMPLE 8

An aluminum bromohydrate is prepared by immersing 59 grams a reactive aluminum in of 307 grams of water and 162 grams of hydrobromic acid and containing the reaction until an aluminum to bromine ratio of 2.0:1 is obtained. It is preferable to provide cooling.

EXAMPLE 9

An aluminum fluorohydrate is prepared by immersing a reactive aluminum of 54 grams in 307 grams of water and 40 grams of hydrofluoric acid and providing cooling. A teflon lined reactor is preferable.

EXAMPLE 10

A stable hydroxyl augmented aluminum chlorohydrate is formed by taking 150 grams of the aluminum chlorohydrate of Example 1 and combining it with 40 grams of the oxygen-bearing aluminum complex of application Ser. No. 176,907 and 40 grams of methanol. After the mixture is heated to approximately 200° F a stable product is obtained. This product is soluble in alcohol.

EXAMPLE 11

An hydroxyl augmented aluminum chlorohydrate is obtained by adding to 150 grams of the aluminum chlorohydrate of Example 1 40 grams of the aforementioned oxygen-bearing aluminum complex, which is an aluminum complex including hydroperoxy groups. After mixing, the combination is left for 24 hours. Then, 10 grams of ethanol are added to the liquor and a reactive aluminum is immersed therein for between 12 to 24 hours. The resulting product is an aluminum oxychlorohydrate which is soluble in alcohol.

EXAMPLE 12

Example 12 is repeated except that no reactive aluminum is used after the ethanol has been added.

EXAMPLE 13

When the procedure of any of Examples 1 to 12 is repeated for an aluminum having a purity of at least 99.99% a purer product having a superior quality and preferable for pharmaceutical and like applications is obtained.

Examples 1 to 12 will result in elemental mercury at the bottom of the reactor. This mercury can be easily avoided by standard techniques for recovery the desired product. But, some mercury may be held in the liquor obtained and may be highly undesirable. A further step can be used to purge the mercury from the liquor. The purging can be accomplished by using a reactive aluminum having 500 to 2000 parts per million. Such a reactive aluminum accumulates and holds mercury so that the liquor purity is remarkably improved.

Having thus described the invention, what I claim as new and desire to be secured by Letters Patent, is as follows:

1. A method of preparing a polymeric aluminum halohydrate having a ratio of aluminum to halogen of from 2:1 to 2.7:1 and a stable pH of from about 4.2 to about 4.3 which comprises:

reacting, in an aqueous medium, a gaseous halogen selected from chlorine, bromine and iodine with mercury permeated aluminum of a purity of at least 99.98% by weight, the mercury content of said mercury permeated aluminum ranging from about 0.1 percent to about 5 percent by weight;

and collecting the formed aluminum halohydrate.

2. The method of claim 1, wherein said mercury permeated aluminum has a mercury content ranging from about 2 percent to about 3 percent by weight.

3. The method of claim 1 wherein said aluminum has a purity of at least 99.99 percent.

4. The method of claim 1, wherein the reaction is carried out at a temperature below 100° F.

5. The method of claim 1, wherein said mercury permeated aluminum is prepared by permeating aluminum in the presence of a hydrogen ion source with mercury.

* * * * *